(12) United States Patent  (10) Patent No.: US 9,207,468 B2
Davalos et al.  (45) Date of Patent: Dec. 8, 2015

(54) PERSONAL PROTECTION EQUIPMENT VERIFICATION

(75) Inventors: Pedro Davalos, Plymouth, MN (US); Kwong Wing Au, Bloomington, MN (US); Saad J. Bedros, West St. Paul, MN (US); Sharath Venkatesha, Golden Valley, MN (US)

(73) Assignee: Honeywell International Inc., Morristown, NJ (US)

( * ) Notice: Subject to any disclaimer, the term of this patent is extended or adjusted under 35 U.S.C. 154(b) by 211 days.

(21) Appl. No.: 13/436,279

(22) Filed: Mar. 30, 2012

(65) Prior Publication Data

US 2013/0257622 A1 Oct. 3, 2013

(51) Int. Cl.
*G08B 21/00* (2006.01)
*G08B 29/00* (2006.01)
*G08B 23/00* (2006.01)
*G05B 11/01* (2006.01)
*G02C 11/00* (2006.01)
*F16P 1/00* (2006.01)
*F16P 3/00* (2006.01)
*G01J 1/02* (2006.01)
*A61F 9/02* (2006.01)

(52) U.S. Cl.
CPC . *G02C 11/10* (2013.01); *F16P 1/00* (2013.01); *F16P 3/00* (2013.01); *G01J 1/0238* (2013.01); *A61F 9/029* (2013.01)

(58) Field of Classification Search
CPC .......... A61F 9/029; G02C 11/10; F16P 1/00; F16P 3/00; G05B 9/02; G01J 1/0238; G02B 27/017; G06F 3/013; G08B 21/02; G08B 21/182; E04G 21/32
USPC ............ 340/635, 5.6, 573.1, 539.1, 572, 556, 340/565, 600, 5.1, 5.74, 539.11; 702/189; 307/326, 328; 361/179, 180
See application file for complete search history.

(56) References Cited

U.S. PATENT DOCUMENTS

| 5,796,341 A * | 8/1998 | Stratiotis ................. 340/573.1 |
| 2004/0004547 A1* | 1/2004 | Appelt et al. ............. 340/573.1 |
| 2009/0147215 A1* | 6/2009 | Howell et al. ............ 351/158 |
| 2010/0110368 A1* | 5/2010 | Chaum ..................... 351/158 |
| 2011/0288659 A1* | 11/2011 | Nelson et al. ............. 700/21 |

* cited by examiner

*Primary Examiner* — Mirza Alam
(74) *Attorney, Agent, or Firm* — Brooks, Cameron & Huebsch, PLLC

(57) ABSTRACT

Systems, methods, and computer-readable and executable instructions are provided for detecting a use of personal protective equipment (PPE). Detecting a use of PPE can include collecting contact data from a number of touch sensitive sensors attached to the PPE. Furthermore, detecting a use of PPE can include determining if the PPE is in proper use based on the collected contact data.

16 Claims, 3 Drawing Sheets

PERSONAL PROTECTION EQUIPMENT VERIFICATION

TECHNICAL FIELD

The present disclosure relates to detecting use of personal protective equipment.

BACKGROUND

Despite the availability and effectiveness of personal protective equipment (PPE) (e.g., safety glasses such as goggles, hard hats, ventilation masks, gloves, etc.), the US Centers for Disease Control and Prevention report that each day more than 100 eye injuries occur on the job. On the job injuries can result in lost time at work, significant financial losses to employers, employees, and/or society through long-term disability, and/or human suffering. Some of these losses from on the job eye injuries can be prevented by proper use of PPE such as safety goggles.

Mandated compliance with workplace safety rules may not be enforced effectively. For example, in general a supervisor physically walks around a manufacturing floor to verify an employee has the proper PPE. This approach can be time intensive and inaccurate, as it does not verify PPE usage for users outside the visual range of the supervisor.

DETAILED DESCRIPTION

Methods and systems for detecting use of personal protective equipment (e.g., safety glasses, safety goggles, gloves, hard hats, masks, among others) are described herein.

Personal protective equipment (PPE) does not provide a benefit unless they are utilized in a designated manner (e.g., worn properly). Therefore, verifying that PPE are present is not enough to decrease the occurrence of injuries. It is advantageous to verify that PPE are present and are properly worn (e.g., covering the proper area of the user).

The embodiments of the present invention can reduce manpower in manual verification, reduce error in a manual inspection process, decrease injuries, reduce costs associated with injuries, and/or combinations thereof. This can be accomplished, for example, by collecting contact data from a number of touch sensitive sensors attached to the PPE and determining if the PPE is in use (e.g., proper use as intended), based on the collected contact data.

Figure 1:
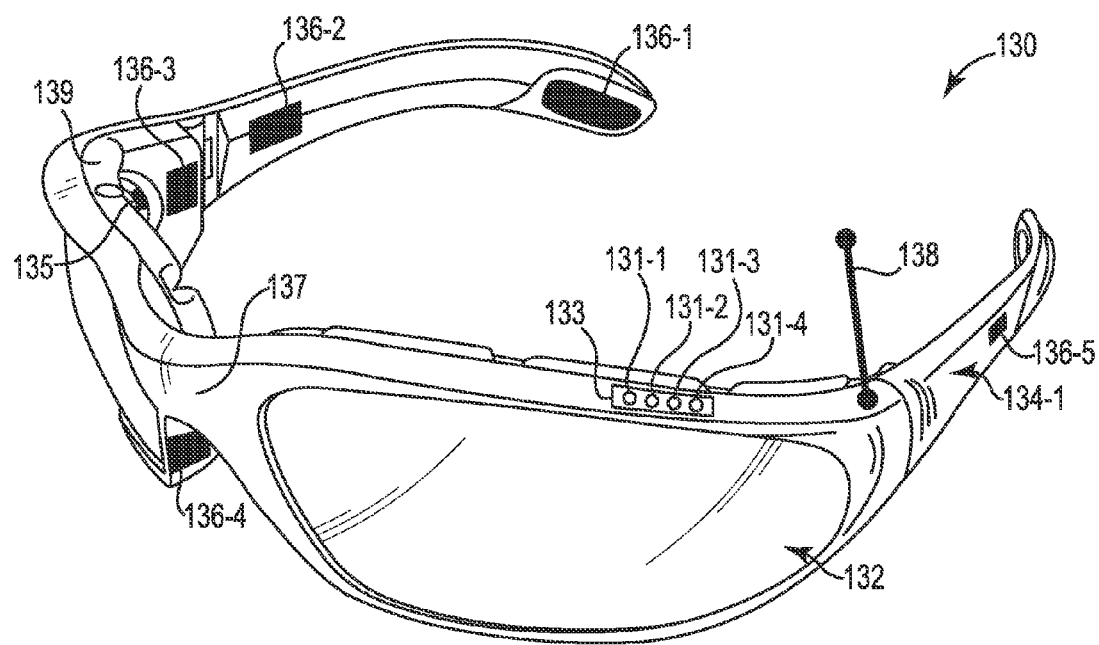
FIG. 1 illustrates a pair of personal protective equipment (PPE) goggles in accordance with one or more embodiments of the present disclosure.

FIG. 1 illustrates a pair of personal protective equipment (PPE) goggles 130 in accordance with one or more embodiments of the present disclosure. PPE goggles can be various types (e.g., goggles, spectacles, wraps, etc) that protect a user from various dangers to the eyes (e.g., lasers, bright light, dust, shrapnel, etc.).

The PPE goggles 130 can comprise a frame 134 that can be a single piece or multiple pieces made of various materials (e.g., plastic, metal, fiberglass, etc.) depending upon the utilization.

The PPE goggles 130 can also comprise lenses 132. The lenses 132 can comprise various materials (glass, plastics, etc.) with various properties (e.g., rated for a specific optical density, shatter resistant, strength, rated for a specific range of wavelengths, rated for dual wavelength ranges, rated for IR radiation, etc.). The lenses 132 can protect a user from various eye injuries including, but not limited to: light exposure, laser exposure, dust exposure, shrapnel exposure, among others.

The PPE goggles 130 can further comprise a number of touch sensitive sensors 136-1, 136-2, 136-3, 136-4, . . . , 136-5 that are attached to various locations (e.g., nose pads, inside of the frame, pads surrounding the eye, etc.) of the PPE goggles 130. For example, a touch sensitive sensor 136-1 could be located on the inside of the frame of the PPE goggles 130 near a location that could contact a user's skin near the user's ear if the PPE goggles 130 were in proper use. In another example, a touch sensitive sensor 136-2 can be located on the inside of the frame of the PPE goggles near a location that could contact a user's skin near the user's temple if the PPE goggles 130 were in proper use.

The PPE goggles 130 can also comprise a set of protective pads 139 that surround the eyes. The protective pads 139 can help further protect the user from various dangers (e.g., dust, light, smaller objects, irritants, etc.). The protective pads 139 can have an attached touch sensitive sensor 136-3 located on various portions of the protective pads (e.g., portion that comes into contact with the skin of the user when in use).

The PPE goggles 130 can have a bridge 137. The bridge 137 can form around the nose of the user when the PPE goggles 130 are in proper use. The bridge 137 can be used to rest the goggles on the nose of the user. The bridge 137 can comprise nose pads that can be used for comfort and/or for keeping the PPE goggles 130 in a desired location (e.g., a location that protects the eyes of the user, etc.). The touch sensitive sensor 136-4 can be attached to the nose pads of the PPE goggles 130. The touch sensitive sensor 136-4 can make contact with the skin on the nose of the user when the PPE goggles 130 are in proper use.

The PPE goggles 130 can comprise multiple touch sensitive sensors 136-1, 136-2, 136-3, . . . , 136-4 at various locations to ensure that the PPE goggles 130 are in use (e.g., proper use, use that protects the eyes of the user, use that PPE is designed for, use that is instructed by manufacturer, etc.) when the touch sensitive sensors 136-1, 136-2, 136-3, . . . , 136-4 are in contact with the user. For example a PPE in proper use can include utilizing the PPE goggles 130 in a way that is likely to protect the user from danger to the user's eyes (e.g., an intended use, etc.). In an example of the PPE goggles 130 with multiple touch sensitive sensors 136-1, 136-2, 136-3, . . . , 136-4, it can be determined that a threshold number of the sensors (e.g., 2, 3, etc.) are needed to be in contact with the skin of the user to determine that the PPE goggles 130 are in an intended use.

In addition, the locations of the touch sensitive sensors that are in contact with the skin can also be important criteria for the determination of proper PPE use. For example, the contact sensitive sensor 136-4 may be in contact with the skin ensuring that the goggle is resting on the nose for proper use. On the other hand, when the contact sensitive sensor 136-5 is in contact with skin, a determination can be made that the PPE is not in proper use. In this case, the user may be holding the goggles or the goggles may be in a user's pocket. In some cases the contact sensitive sensor 136-5 must be out of contact with the user for a determination to be made that the PPE is in proper use.

The PPE goggles 130 can also comprise a communication device 138. The communication device 138 can utilize a variety of communication techniques (e.g., WiFi, Bluetooth, local area network, wide area network, mobile network, among others). Communication device 138 can have an antenna to increase the signal strength of the communication. Communication device 138 can also comprise an internal antenna, and is shown as an external antenna for display purposes. The communication device 138 can transfer information about the status (e.g., in contact with skin, not in contact with skin, power on, power off, etc.) of the touch sensitive sensors 136-1, 136-2, 136-3, . . . , 136-4.

The communication device can also transfer (e.g., send to a computing device, etc.) specification information about the PPE goggles 130. Specification information can include the intended purpose (e.g., protected range of wavelengths, intensity of light, strength of lenses, etc.) of the PPE goggles. The specification information can enable a computing device to determine if the user is safe when entering a restricted area by comparing the specification information of the PPE goggles 130 with information about the restricted area. Information about the restricted area can include the dangers to users of the restricted area (e.g., laser wavelength in use, type of welding equipment, type of lasers, etc.).

The PPE goggles can comprise a display 133. The display 133 can comprise various types of visual displays to alert the user when a touch sensitive sensor 136-1, 136-2, 136-3, . . . , 136-4 is in contact with the user and/or when a touch sensitive sensor 136-1, 136-2, 136-3, . . . , 136-4 is not in contact with the user. For example, the display 133 can comprise lights 131-1, 131-2, 131-3, . . . , 131-4 that can correspond to the number of touch sensitive sensors 136-1, 136-2, 136-3, . . . , 136-4. In some embodiments when a light is on, that could indicate to the user that a particular sensor is in contact with the user's skin. The display 133 can indicate to other people in the area (e.g., supervisor, safety team, etc) that a particular user is not in contact with a number of the touch sensitive sensors 136-1, 136-2, 136-3, . . . , 136-4. For example, if there are multiple users and PPE goggles for each user, a supervisor could determine which user is not in contact with all of the touch sensitive sensors 136-1, 136-2, 136-3, . . . , 136-4 and further determine if there is a technical issue with the touch sensitive sensors and/or if the user is not wearing the PPE goggles 130 properly (e.g., in a way that ensures protection of the user).

The display 133 can also be utilized for other functions. For example, a computing device could send signals to the display 133 to notify the user of different issues that the computing device is detecting. For example, if the display 133 were lights 131-1, 131-2, 131-3, . . . , 131-4, the computing device could send a signal to the display 133 to create a signal with the lights 131-1, 131-2, 131-3, . . . , 131-4 that can be identified by the user. In an example, the computing device could have a single light 131-1 blink repeatedly in order to indicate that the user was not in contact with a particular sensor 136-1. In a different example, the computing device could create a signal for the user choosing a pair of PPE goggles 130 that do not have the correct specifications for a particular restricted area by making all or some of the lights blink repeatedly.

The PPE goggles 130 can also include a number of various other sensors (e.g., light sensitive sensors 135, temperature sensors, etc.). For example, the PPE goggles 130 can comprise a number of touch sensitive sensors as described herein and also comprise a number of light sensitive sensors 135.

The light sensitive sensors 135 can be placed in various locations on the PPE goggles 130. For example, the light sensitive sensors 135 could be placed near the lenses 132 and the protective pads 139. The light sensitive sensors could be placed in a location on the PPE goggles 130 where proper use of the PPE goggles 130 would change the intensity of light enough for the light sensitive sensors 135 to detect the change. For example, the light sensitive sensors 135 could be placed in a location that would change the light intensity when the protective pads 139 are flush up against the users skin, creating a space between the eye of the user and the inside portion of the lenses 132 that changes light intensity when in proper use.

In another example, not shown, the PPE can be a hard hat and/or protective head gear. The PPE hard hat can include a number of touch sensitive sensors in a number of locations that could be in contact with the skin of the user when in proper use. For example, a touch sensitive sensor could be located at the top of the inside portion of the PPE hard hat, so only when the PPE hard hat is securely placed on the user's head will the touch sensitive sensor make contact with the head of the user.

The PPE hard hat can further include a number of touch sensitive sensors in a number of locations that are not in contact with the user when the PPE hard hat is in proper use. For example, a number of touch sensitive sensors can be located on the exterior portions of the PPE hard hat. In this example, it is possible to place the number of touch sensitive sensors in locations that are commonly used for carrying the PPE hard hat. If the number of touch sensitive sensors located on the exterior portions of the PPE hard hat are in contact with the user, it can be determined that the PPE hard hat is not in proper use.

The PPE hard hat can include a display and a communications device similar to the display and the communications device for the PPE goggles shown in FIG. 1.

In a further example, not shown, the PPE device can be a mask to protect a user's face and or respiratory system. The PPE mask can comprise similar features as described herein. For example, the PPE mask can comprise a number of touch sensitive sensors, wherein a portion of the touch sensitive sensors can be in contact with the user and a portion of the touch sensitive sensor are not in contact (e.g., out of contact, etc.) when the PPE mask is in proper use.

The number of touch sensitive sensors that can be in contact with the user can be located near where the PPE mask makes contact with the user's face. For example, the PPE mask could make contact with the user's in order to create a seal from exterior contaminants (e.g., dust, sand, etc.). The number of touch sensitive sensors could be located near the seal to make contact with the face of the user.

The number of touch sensitive sensors that are not in contact with the user when the PPE mask is in proper use can be located at a number of locations. For example, the number of touch sensitive sensors that are not in contact with the user when the PPE mask is in proper use can be located near a handle that is used to carry the PPE mask when not in use. In another example, the number of touch sensitive sensors that are not in contact with the user when the PPE mask is in proper use can also be located at locations that would make contact with the user's head when the PPE mask is worn improperly on the top of the head of the user.

The PPE mask can also include a display and a communications device similar to the display and the communications device for the PPE goggles shown in FIG. 1.

As described herein, the PPE device can include any number of personal protective equipment (e.g., safety glasses, safety goggles, ear plugs, hard hats, safety harness, boots, gloves, jackets, etc.).

Figure 2:
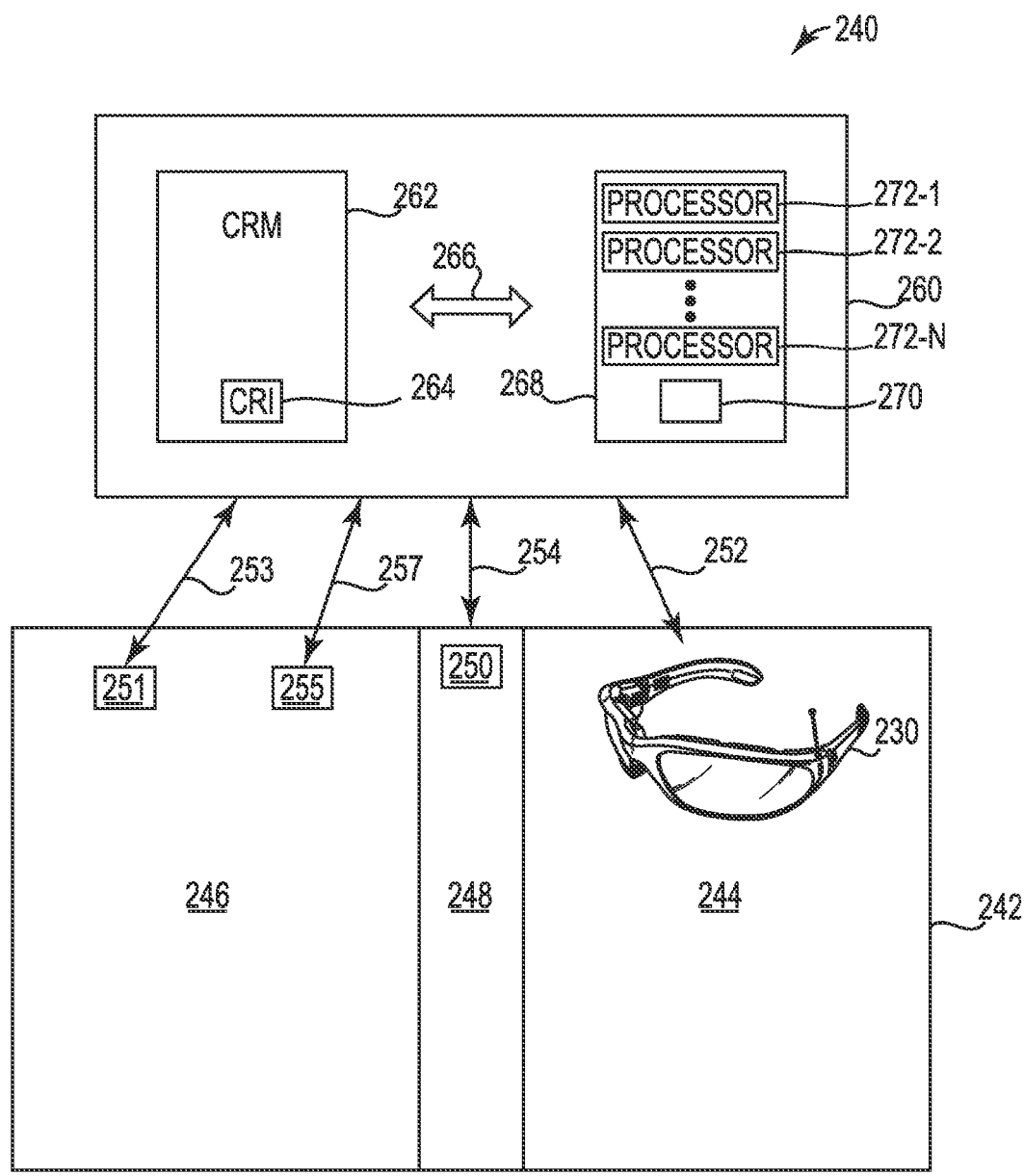
FIG. 2 illustrates a system for detecting use of personal protective equipment (PPE) prior to entering a restricted area in accordance with one or more embodiments of the present disclosure.

FIG. 2 illustrates a system 240 for detecting use of personal protective equipment (PPE) 230 prior to entering a restricted area 246 in accordance with one or more embodiments of the present disclosure. In the system 240 the PPE 230 can comprise various protective equipment (e.g., safety goggles, gloves, boots, hard hats, etc). For example, the PPE 230 can be the PPE goggles 130 previously described in FIG. 1. The PPE 230 can be communicatively couple to a computing device 260. The PPE 230 can collect and send data regarding the attached touch sensitive sensors to the computing device 260.

The system 240 can include a non-restricted area 244. The non-restricted area 244 can include an area that does not pose significant danger to the user without the use of the PPE 230. For example, if the PPE 230 is a pair of PPE goggles used to protect a user from a harmful laser, the non-restricted area 244 would not have areas that included exposure to the harmful laser. Having a non-restricted area can allow the user time to put on the PPE 230 and perform checks to ensure that the PPE 230 is properly in use. For example, if the PPE 230 is a pair of PPE goggles 130, the non-restricted area could be used to ensure that the PPE goggles are in proper use by the user in order to protect the user from danger within a restricted area 246.

The system 240 can include a door 248 that restricts access to the restricted area 246 and can also act as a barrier to any dangerous circumstances (e.g., lasers, welding light, dust, sharp objects, etc.) that are found within the restricted area 246. Attached to the door 248 can be a locking mechanism 250. The locking mechanism 250 can lock the door to prevent the user from accessing the restricted area 246. The locking mechanism 250 can be communicatively coupled 254 to the computing device 260. The computing device 260 can control the locking mechanism 250 (e.g., engage the locking mechanism, release the locking mechanism, etc.). The computing device 260 can determine if the PPE 230 is in proper use prior to unlocking the locking mechanism 250. If the computing device determines that the PPE 230 is not in proper use, then the door 248 can remain locked via the locking mechanism 250.

If it is determined by the computing device 260 that the PPE 230 is in proper use by the user, then the locking mechanism can be unlocked and the user can be allowed to enter the restricted area 246. The computing device can continue to receive communication 252 (e.g., WiFi, Bluetooth, LAN, WAN, radio frequency, etc.) from the PPE 230 after the user and PPE 230 have entered the restricted area 246. The computing device 260 can determine that the PPE 230 is no longer in proper use when the PPE 230 is located within the restricted area 246. If it is determined by the computing device 260 that the PPE 230 is no longer in proper use, the computing device 260 can respond in a variety of ways. For example, the computing device 260 can issue a warning to the user that the PPE 230 is no longer in proper use.

In another example, if it is determined that the PPE 230 is no longer in proper use, the computing device 260 can disable a work device 251. A work device 251 can be a variety of devices (e.g., a laser, a welding device, a saw, etc.) that can be potentially harmful to a user if the PPE 230 is not in proper use. The computing device 260 can disable the work device 251 in a variety of ways. For example, the computing device 260 can be communicatively coupled to the work device 251 and send a signal 253 (e.g., WiFi, Bluetooth, LAN, WAN, radio frequency, etc.) to the work device 251 to disable the work device 251. In another example, the computing device 260 can disable a power supply to the work device 251 in order to disable the work device 251.

In another example, if it is determined that the PPE 230 is no longer in proper use, the computing device 260 can enable a safety device 255. The safety device 255 can be a variety of safety devices (e.g., vacuum hood, fire extinguishers, power supply shut off, emergency lights, intercom, alarm, etc.). The computing device 260 can be communicatively coupled 257 to the safety device 255. The computing device 260 can also alert the user that the PPE 230 is no longer in proper use. The computing device 260 can alert the user in a variety of ways including, but not limited to: an intercom alerting all occupants of the area, an intercom indicating a specific PPE that is no longer in proper use, alerting a safety team member to instruct the user and/or all occupants, among others.

The computing device 260 can receive specification information about the PPE 230. As described herein, specification information can include the intended purpose of the PPE 230. The specification information can enable the computing device 260 to determine a safety status for the user. The safety status can include a determination by the computing device 260 utilizing safety information including, but not limited to: number of touch sensitive sensors are in contact with the user, specification information of the PPE 230, information about the restricted area 246, among other safety information.

Information about the restricted area 246 can include the dangers to users of the restricted area 246 (e.g., laser wavelength in use, type of welding equipment, type of lasers, etc.). The safety status can be used to determine if the user will be permitted access to the restricted area 246. For example, even if the user is in contact with all of the touch sensitive sensors, the computing device 260 can determine that the specification information received about the PPE 230 will not sufficiently protect the user from dangers within the restricted area 246. For example, the PPE 230 could be a pair of PPE goggles 130 designed to protect a user from a specific range of wavelengths and the restricted area 246 may utilize a laser that produces wavelengths outside the range of wavelengths that the PPE goggles 130 protect against. If the previous example information was received by the computing device 260, it could lead the computing device 260 to determine that the safety status is not acceptable and the user may not be allowed access to the restricted area 246.

If the safety status is determined to be acceptable by the computing device 260, then the computing device 260 can allow access to the restricted area 246 as described herein.

The computing device 260 can also include a computer readable medium (CRM) 262 in communication with processing resources 272-1, 272-2, . . . , 272-N. CRM 262 can be in communication with a device 268 (e.g., a Java® application server, among others) having processor resources 272-1, 272-2, . . . , 272-N. The device 268 can be in communication with a tangible non-transitory CRM 262 storing a set of computer-readable instructions (CRI) 226 executable by one or more of the processor resources 272-1, 272-2, . . . , 272-N, as described herein. The CRI 226 can also be stored in remote memory managed by a server and represent an installation package that can be downloaded, installed, and executed. The device 268 can include memory resources 270, and the processor resources 272-1, 272-2, . . . , 272-N can be coupled to the memory resources 270.

Processor resources 272-1, 272-2, . . . , 272-N can execute CRI 226 that can be stored on an internal or external non-transitory CRM 262. The processor resources 272-1, 272-2, . . . , 272-N can execute CRI 226 to perform various functions, including the functions described in FIG. 2. For example, the processor resources 272-1, 272-2, . . . , 272-N can execute CRI 226 to determine if the PPE 230 is in proper use based upon received contact data. A non-transitory CRM (e.g., CRM 262), as used herein, can include volatile and/or non-volatile memory. Volatile memory can include memory that depends upon power to store information, such as various types of dynamic random access memory (DRAM), among others. Non-volatile memory can include memory that does not depend upon power to store information. Examples of non-volatile memory can include solid state media such as flash memory, electrically erasable programmable read-only memory (EEPROM), phase change random access memory (PCRAM), magnetic memory such as a hard disk, tape drives, floppy disk, and/or tape memory, optical discs, digital versatile discs (DVD), Blu-ray discs (BD), compact discs (CD), and/or a solid state drive (SSD), etc., as well as other types of computer-readable media.

The non-transitory CRM 262 can be integral, or communicatively coupled, to a computing device, in a wired and/or a wireless manner. For example, the non-transitory CRM 262 can be an internal memory, a portable memory, a portable disk, or a memory associated with another computing resource (e.g., enabling CRIs to be transferred and/or executed across a network such as the Internet).

The CRM 262 can be in communication with the processor resources 272-1, 272-2, . . . , 272-N via a communication path 266. The communication path 266 can be local or remote to a machine (e.g., a computer) associated with the processor resources 272-1, 272-2, . . . , 272-N. Examples of a local communication path 266 can include an electronic bus internal to a machine (e.g., a computer) where the CRM 262 is one of volatile, non-volatile, fixed, and/or removable storage medium in communication with the processor resources 272-1, 272-2, . . . , 272-N via the electronic bus. Examples of such electronic buses can include Industry Standard Architecture (ISA), Peripheral Component Interconnect (PCI), Advanced Technology Attachment (ATA), Small Computer System Interface (SCSI), Universal Serial Bus (USB), among other types of electronic buses and variants thereof.

The communication path 266 can be such that the CRM 262 is remote from the processor resources e.g., 272-1, 272-2, . . . , 272-N, such as in a network connection between the CRM 262 and the processor resources (e.g., 272-1, 272-2, . . . , 272-N). That is, the communication path 266 can be a network connection. Examples of such a network connection can include a local area network (LAN), wide area network (WAN), personal area network (PAN), and the Internet, among others. In such examples, the CRM 262 can be associated with a first computing device and the processor resources 272-1, 272-2, . . . , 272-N can be associated with a second computing device (e.g., a Java® server, etc.). For example, a processing resource 272-1, 272-2, . . . , 272-N can be in communication with a CRM 262, wherein the CRM 262 includes a set of instructions and wherein the processing resource 272-1, 272-2, . . . , 272-N is designed to carry out the set of instructions for detecting use of PPE.

The processor resources 272-1, 272-2, . . . , 272-N coupled to the memory 226 can enable/disable various devices (e.g., locking mechanism device 250, work device 251, safety device 255, among others).

The processor resources 272-1, 272-2, . . . , 272-N coupled to the memory 226 can receive data collected by the number of touch sensitive sensors. The processor resources 272-1, 272-2, . . . , 272-N coupled to the memory 226 can also determine a number of sensors that are in contact with a user from the data. The processor resources 272-1, 272-2, . . . ,
272-N coupled to the memory 226 can also allow access to the restricted area if the number of sensors in contact with the user is above a predetermined threshold, wherein to allow access includes a release of the locking mechanism. The processor resources 272-1, 272-2, . . . , 272-N coupled to the memory 226 can also issue a warning to the user if the number of sensors lose contact with user. Furthermore, the processor resources 272-1, 272-2, . . . , 272-N coupled to the memory 226 can disable a device if the number of sensors lose contact with user, wherein the device is a hazard to the user if the PPE goggles are not worn properly.

As used herein, "logic" is an alternative or additional processing resource to execute the actions and/or functions, etc., described herein, which includes hardware (e.g., various forms of transistor logic, application specific integrated circuits (ASICs), etc.), as opposed to computer executable instructions (e.g., software, firmware, etc.) stored in memory and executable by a processor.

Figure 3:
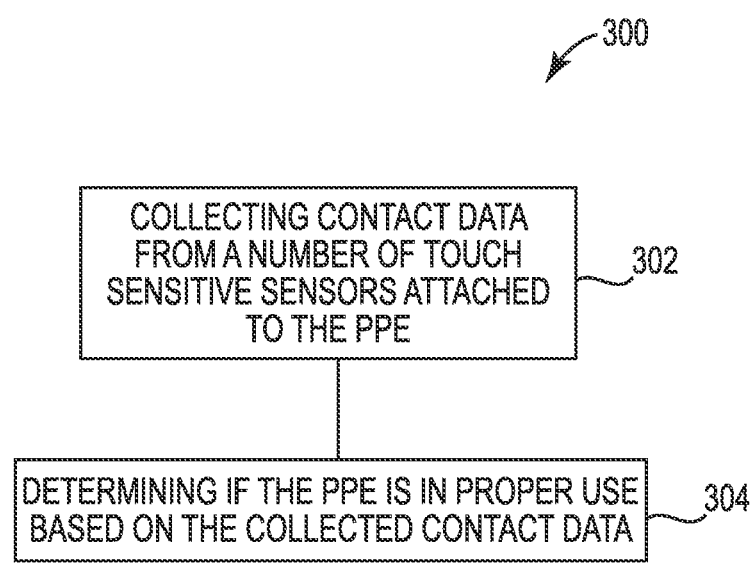
FIG. 3 illustrates a method for detecting use of personal protective equipment (PPE) in accordance with one or more embodiments of the present disclosure.

FIG. 3 illustrates a method 300 for detecting a use of a PPE in accordance with one or more embodiments of the present disclosure. PPE can include various types and models of personal protective equipment (e.g., safety goggles, safety glasses, hard hats, gloves, among others).

At 302 data is collected from a number of touch sensitive sensors attached to the PPE. Touch sensitive sensors can include a variety of sensors that recognize a physical contact. For example, touch sensitive sensors can recognize the physical contact of a user's skin.

Touch sensitive sensors can include technology found in touch screen displays. For example touch sensitive sensors can include technology such as, resistive screen technology, capacitive screen technology, infrared (IR) screen technology, and surface acoustical wave (SAW) screen technology, among others. With each of the screen technologies there can be benefits and limitations including but not limited to: durability, accuracy, application, interferences, among others.

Touch sensitive sensors can detect if the touch sensitive sensor is in contact with the user. The touch sensitive sensors can send a signal (e.g., positive reading) if they are in contact with a user and send a different signal (e.g., negative reading, no reading, etc) if they are not in contact with the user.

The touch sensitive sensors can be attached to the PPE in a variety of locations depending on the type and model of the PPE. The touch sensitive sensors can be attached at strategic locations to ensure that the user is wearing the PPE in a proper fashion (e.g., recommended use, use that better protects the user, etc.). For example, it can be determined that touch sensitive sensors could be attached to the nose pads on a pair of PPE goggles. This could ensure that the goggles were worn in a proper fashion (e.g., so the nose pads are located on the user's nose) as opposed to a non-proper fashion (e.g., worn on top of the user's head, worn so the PPE goggles were not protecting the user's eyes, etc).

At 304, it is determined if the PPE is in proper use by the user based on the collected contact data from the attached touch sensitive sensors. Data can be collected from the touch sensitive sensors by a communicatively coupled computing device. For example, the touch sensitive sensors can be designed to transmit a positive signal if it is in contact with the user and/or transmit a negative signal if it is not in contact with the user.

The positive signal can be a variety of signals and/or indications to the computing device that the touch sensitive sensor is in contact with the user. The negative signal can be a variety of signals or no signal to indicate the touch sensitive sensor is not in contact with the user.

Multiple touch sensitive sensors can be utilized for a single PPE. For example, if the PPE were a pair of PPE goggles, touch sensitive sensors can be placed on the nose pads and on the sides where the goggles should make contact with the user's head.

It can be determined (e.g., via computing device, via a user of a display, etc.) that the PPE is in proper use through the utilization of multiple touch sensors. For example, if data is sent to a computing device from multiple sensors, the computing device can determine how many of the sensors are in contact with the user.

It can be determined that if a number of the multiple touch sensitive sensors are not in contact with the user that the PPE is not in proper use. For example, if there are two touch sensitive sensors on a pair of PPE goggles, both of the sensors may have to send a positive signal for the computing device to determine that the PPE goggles are in proper use. In the same example, it could be that the user is not in contact with the touch sensitive sensors because the PPE goggles are not worn properly (e.g., on top of the user's head, worn too low on the nose to fully protect the user, etc.).

If there are multiple touch sensitive sensors on a PPE, it can be determined the locations and a threshold of touch sensitive sensors need to be in contact with the user in order for the computing device to determine that the PPE is in proper use. For example, if the multiple touch sensitive sensors were attached to a pair of PPE goggles, a portion of the touch sensitive sensors could be place on the nose pads of the goggles and a different portion could be placed on the inside of the frame where the frame would be in contact with the skin of the user (e.g., near the temple, near the ear, among other locations).

It could be determined that the threshold of touch sensitive sensors for a PPE with four touch sensitive sensors attached is only two touch sensitive sensors in one area and one touch sensitive sensor on the nose pad to assure the computing device that the PPE is in proper use. For example, if a pair of PPE goggles had two touch sensitive sensors on the nose pads and two touch sensitive sensors on the inside of the frame near the ear of the user, it could be determined that only 3 out of the four sensors would have to be in contact with the user for the computing device to determine that the PPE goggles were in proper use.

A determination that a PPE is in proper use can indicate to the computing device that a designated area is accessible to the user of the PPE. For example, if the computing device determines that the PPE is in proper use, the computing device can allow access to a designated area (e.g., unlock a door). The designated area could be a restricted area, wherein the PPE could be utilized to protect the user from various dangers within the restricted area.

A determination that the PPE is in proper use can also initiate a response by the computing device to disable and/or turn off devices within the restricted area that can be harmful to the user if the PPE is not in proper use. A determination that a PPE is in proper use can further initiate a response by the computing device to enable and/or turn on a safety device that could make the restricted area less harmful to the user when the PPE is not in proper use.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

As used herein, "a" or "a number of" something can refer to one or more such things. For example, "a number of devices" can refer to one or more devices.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A method for detecting a use of personal protective equipment (PPE), comprising:
    collecting contact data from a number of touch sensitive sensors attached to the PPE;
    determining if the PPE is in proper use based on the collected contact data, wherein determining if the PPE is in proper use includes a determination that a portion of the number of touch sensitive sensors are in contact and that a portion of the number of touch sensitive sensors are not in contact, wherein the portion of touch sensitive sensors not in contact include touch sensitive sensors that indicate an improper use when in contact;
    determining safety specifications of the PPE, wherein the safety specifications include protection limits for a number of hazards;
    determining hazard information associated with a restricted area based on a number of devices within the restricted area;
    enabling the number of devices within the restricted area only when the PPE is in proper use and when the protection limits of the PPE are sufficient when compared to the hazard information associated with the restricted area;
    disabling the number of devices within the restricted area when the PPE is within the restricted area and the PPE is not in proper use or when the protection limits of the PPE are not sufficient when compared to the hazard information associated with the restricted area; and
    indicating, via a display including a number of lights corresponding to the number of touch sensitive sensors attached to the PPE, a particular sensor of the portion of the number of touch sensitive sensors that are in contact by turning on a particular light corresponding to the particular sensor.

2. The method of claim 1, wherein the number of touch sensitive sensors are located at a number of locations to ensure an intended use of the PPE.

3. The method of claim 1, wherein determining if the PPE is in proper use includes determining if the PPE is in proper use for an intended purpose of the PPE.

4. The method of claim 1, further comprising:
utilizing a computing device to allow access to restricted area when collected contact data indicates that the PPE is in proper use.

5. The method of claim 4, wherein the method includes alerting, via the computing device, monitors and occupants of the restricted area if collected contact data indicates that the PPE is not in proper use.

6. A machine-readable non-transitory medium storing instructions for detecting use of personal protective equipment (PPE), executable by a machine to cause the machine to:
receive touch sensitive sensor data from a number of touch sensitive sensors attached to the PPE;
determine a number of touch sensitive sensors in contact with a user;
determine a number of touch sensitive sensors not in contact with a user;
receive data for a restricted area and specifications for the PPE, wherein the data for the restricted area includes hazard information based on a number of devices within the restricted area and the specifications for the PPE include protection limits for a number of hazards;
determine a safety status based on an area where the number of touch sensitive sensors are located, the number of touch sensitive sensors in contact with the user, the number of touch sensitive sensors not in contact with the user, the specifications for the PPE, and the data for the restricted area the user intends to access, wherein the number of touch sensitive sensors not in contact with the user include touch sensitive sensors that indicate an improper use when in contact with the user;
enable the number of devices within the restricted area only when the PPE is in proper use and when the protection limits of the PPE are sufficient when compared to the hazard information associated with the restricted area;
disable the number of devices within the restricted area when the PPE is within the restricted area and the PPE is not in proper use or when the protection limits of the PPE are not sufficient when compared to the hazard information associated with the restricted area;
indicate to the user, via a display attached to the PPE including a number of lights corresponding to the number of touch sensitive sensors attached to the PPE, a particular sensor of the number of touch sensitive sensors in contact with the user by turning on a particular light of the number of lights corresponding to the particular sensor; and
notify the user of a safety status.

7. The non-transitory medium of claim 6, wherein notify the user includes allowing access to the restricted area if the safety status is acceptable.

8. The non-transitory medium of claim 6, wherein notify the user includes denying access to the restricted area if the safety status is not acceptable.

9. The non-transitory medium of claim 6, wherein the safety status includes a threshold number of touch sensitive sensors in contact with the user.

10. The non-transitory medium of claim 6, wherein notify the user includes sending a signal to the display attached to the PPE.

11. A system for detecting use of personal protective equipment (PPE) prior to entering a restricted area, comprising:
a pair of PPE goggles having a display including a number of lights;
a number of touch sensitive sensors attached to the PPE goggles, wherein the number of lights of the display corresponds to the number of touch sensitive sensors; and
a computing device communicatively coupled to a locking mechanism restricting access to the restricted area, wherein the computing device comprises a memory and a processor resource coupled to the memory to:
determine safety specifications of the PPE goggles, wherein the safety specifications include protection limits for a number of hazards;
determine hazard information associated with the restricted area based on a number of devices within the restricted area;
receive data collected by the number of touch sensitive sensors;
determine if a number of sensors are in contact with a user based on the data;
enable the number of devices within the restricted area only when the number of sensors are in contact with the user and when the protection limits of the PPE goggles are sufficient when compared to the hazard information associated with the restricted area;
disable the number of devices within the restricted area when the PPE goggles are within the restricted area and the number of sensors are not in contact with the user or when the protection limits of the PPE are not sufficient when compared to the hazard information associated with the restricted area;
indicate, via the display, a particular sensor of the number of touch sensitive sensors that is in contact with the user by turning on a particular light of the number of lights corresponding to the particular sensor; and
release the locking mechanism to allow access to the restricted area only if the number of sensors in contact with the user is above a predetermined threshold.

12. The system of claim 11, wherein a number of light sensors are attached to the PPE goggles.

13. The system of claim 11, wherein the safety specifications of the PPE goggles includes a range of visual protection for the user.

14. The system of claim 11, wherein the processor is further instructed to issue a warning to the user if the number of sensors in contact with user is below the predetermined threshold.

15. The system of claim 11, wherein a selected number of the sensors must be out of contact with the user to grant access to the restricted area.

16. The system of claim 11, wherein the touch sensitive sensors are attached at locations that contact the skin of the user during an intended use of the PPE goggles.

* * * * *